United States Patent [19]

Yoshizawa et al.

[11] Patent Number: 5,028,774
[45] Date of Patent: Jul. 2, 1991

[54] METHOD AND APPARATUS FOR DETECTING AND MEASURING THE REFRACTIVE INDEX OF AN OPTICAL DISC SUBSTRATE

[75] Inventors: Akihiko Yoshizawa; Yoshihiko Masakawa, both of Hachioji, Japan

[73] Assignee: Olympus Optical Co., Ltd., Tokyo, Japan

[21] Appl. No.: 478,318

[22] Filed: Feb. 12, 1990

[30] Foreign Application Priority Data

Feb. 21, 1989 [JP] Japan ............................ 1-40931

[51] Int. Cl.$^5$ ............................................. G02F 1/01
[52] U.S. Cl. ..................................... 250/225; 356/369
[58] Field of Search ................ 250/225; 356/364, 365, 356/366, 367, 368, 370, 128

[56] References Cited

U.S. PATENT DOCUMENTS

3,724,952  4/1973  Vossberg ............................ 356/368
4,053,232 10/1977  Dill et al. ............................ 356/369
4,792,227 12/1988  Yoshizawa ........................... 356/128

*Primary Examiner*—David C. Nelms
*Attorney, Agent, or Firm*—Armstrong, Nikaido, Marmelstein, Kubovcik & Murray

[57] ABSTRACT

A light beam linearly polarized is incident on a substrate for a disc not a right angle, but at an an oblique angle with respect to the substrate surface, while holding constant an angle κ between the plane of polarization of the linearly polarized light and the incident plane, and the intensity of the leaked light passing through an analyzer set in a crossed Nichol state with respect to the linearly polarized light is measured while changing an angle (azimuth angle Ψ) between the incident plane and a reference line, such as a line extending in the radial direction of the disc substrate. These measured values are compared with the calculated values derived from the theoretical formula for determining the respective magnitudes of the three refractive indices.

9 Claims, 11 Drawing Sheets

METHOD AND APPARATUS FOR DETECTING AND MEASURING THE REFRACTIVE INDEX OF AN OPTICAL DISC SUBSTRATE

BACKGROUND OF THE INVENTION

Field of the Invention and Description of the Related Art

This invention relates to a method and an apparatus for detecting and measuring the refractive index of a substrate for an optical disc, which can precisely detect and measure the main axis of an ellipsoid of the refractive index (i.e., an index ellipsoid).

Recently, there has come to be noted an optical information recording and reproducing apparatus whereby information can be recorded at a high density in an optical recording medium by condensing light beams and projecting them onto this recording medium and the recorded information written into the recording medium can be read out (reproduced) at a high speed by receiving with a light detector the light returning from this recording medium.

The above mentioned recording medium is divided into a write-once type in which information cannot be erased after being once written, and a magneto-optical type in which a magnetic layer is formed to make information erasable after once written by utilizing the optical Kerr Effect.

A substrate for the above magneto-optical recording medium may be formed of acrylate resin such as PMMA (polymethyl-methacrylate). This acrylate resin is high in optical characteristics but has a defect in that the hygroscopicity is so high as to deflect the recording medium surface.

Therefore, it is desired to use for the substrate a material which is hard to deflect, high in form stability and high in mechanical strength. It is also desired for this substrate to have good optical characteristics.

As disclosed in U.S. Pat. No. 4,792,227, since light beams are condensed in a substrate of the magneto-optical or other type, double refraction produced in the substrate is responsible for lowering the S/N ratio of a reproduced signal.

The above mentioned substrate for the recording medium is injection-molded in many cases. In these cases, the substrate is more easily susceptible to distortion which will often exhibit double refraction.

The substance showing optical anisotropy generally has the three main refractive indices $N_1$, $N_2$, $N_3$ (or $n_1$, $n_2$, $n_3$) in different directions orthogonal to one another. The ellipsoid defined by these three main axes is an ellipsoid of the refractive index.

The degree of the above mentioned double refraction can easily be known from the status of the index ellipsoid for the substance.

Figures 1, 2:
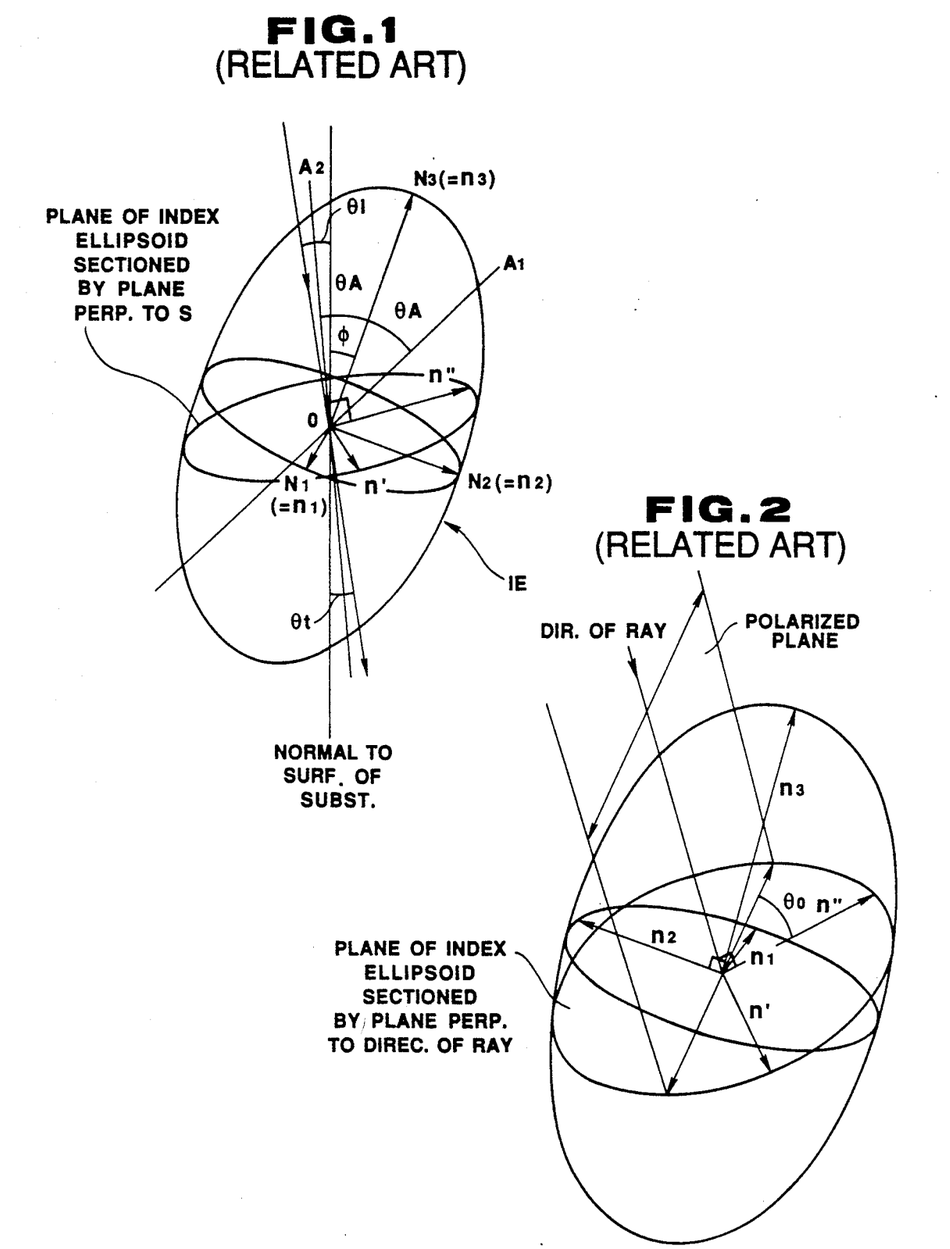
FIGS. 1 through 3 are explanatory views showing the index ellipsoid and other elements, based on the above publication of the related art, necessary for determining the light intensity to determine the three main refractive indices.

Assuming that a ray (light beam) propagates in the direction of S, as shown in FIG. 1, the plane of the index ellipsoid IE sectioned by a plane perpendicular to S and passing the center O of the index ellipsoid IE is generally an ellipse. The difference between the long (major) axis and the short (minor) axis of this ellipse corresponds to the degree of double refraction. The optical axis refers to a direction of a ray when the above sectioned plane becomes a circle. In this case, no double refraction will occur.

If the substrate is of a uniaxial crystal, the above sectioned plane becomes a circle only in one direction. If the substrate is of a biaxial crystal, the sectioned plane becomes a circle, in two directions. These two directions are indicated by $A_1$, $A_2$ in FIG. 1. In the plane including $A_1$, $A_2$, the direction in which the angle between $A_1$ and $A_2$ is divided into two equal angles $\theta_A$ represents a direction of one main refractive index $N_3$ among the three main refractive indices. The directions of the remaining two main refractive indices $N_1$, $N_2$ lie in the planes perpendicular to the direction of $N_3$.

For a PC (polycarbonate) plate injection-molded for the optical disc, the magnitudes of $N_1$ and $N_2$ are almost equal to each other, while the magnitude of $N_3$ is larger than the magnitudes of $N_1$ and $N_2$. The resulting index ellipsoid has a shape of a Rugby ball. Furthermore, $N_3$ shows optical anisotropy substantially perpendicular to the surface of the disc substrate. The fact mentioned above is already known is described in the following paper by the inventor: Akihiko Yoshizawa, "An Analysis of Optical Anisotropy of PC Substrate for Magneto-Optical Disc", Optics, Vol. 15, No. 3 (1986), referred to as Reference 1 hereinafter.

For the reason, the status of the index ellipsoid is not known at all in the conventional method of measuring double refraction with a normal incident ray. In an actual optical pick-up using condensed rays with different incident angles, therefore, how the degree of double refraction will affect a reproduced signal cannot be determined.

Generally, the directions of the three main refractive indices, i.e., the mains axes of the index ellipsoid, and the magnitudes or lengths thereof have to be known in order to determine the status of the index ellipsoid. For a the substrate of the optical disc, it sometimes happen that while the directions of the main axes are almost known, their magnitudes are a problem to determine. One method of determining those magnitudes is disclosed in the above cited U.S. Pat. No. 4,792,227. This method is also explained in detail in the above cited Reference 1 by the inventor. Because this method basically relies on a magneto-optical head actually employed, the plane of polarization of an incident linearly polarized light is fixed to be normal to the radius of the disc, and hence the angle between the incident plane and the polarized plane is varied upon changes of an azimuth. (In contrast, the angle between the incident plane and the polarized plane will be fixed to a certain angle in this embodiment.) While a uniaxial model has been supposed in the above cited U.S. patent, a biaxial model is required for more precise measurement.

Therefore, the theoretical formulae will be rewritten below so as to be match with the biaxial model.

FORMULAE FOR CALCULATING THE DEGREE OF ELLIPTICITY WHERE POLARIZED LIGHT IMPINGES ON SUBSTRATE SHOWING BIAXIAL CHARACTERISTICS (1) Premises I, II and Definition of Parameters III As with the appendix 1 of the above cited Reference 1, calculation formulae will be derived by presupposing two premises below.

(I) The intersecting line between the interface (disc surface) and the plane of polarization of the incident ray is normal to the radial direction of the disc (this premised is to be matched with the setting of the above mentioned experiment).

(II) When the index ellipsoid is considered in the biaxial model, two of the three main refractive indices are parallel to the radial direction and lie in the plane normal to the disc surface.

This presupposes that the index ellipsoid is inclined only in the radial direction.

(III) Definition of Parameters $\theta_o$: angle between the refractive index n" (or n') and the polarized plane in the sectioned plane of the index ellipsoid, $\theta$: angle between the polarized plane and the direction of a long axis of the ellipsoid as viewed in the direction of the transmitted ray, $\alpha$: phase difference, $\Psi$: angle between the incident plane and the radial direction, $\theta i$: incident angle, $\theta t$: angle between the normal to the disc surface and the long axis of the ellipsoid after refraction, $\phi$: angle between the normal to the disc surface and the long axis of the ellipsoid in the radial direction.

(2) Long- to Short-Axis Ratio of Elliptically Polarized Ray

When the long axis is assumed to have a length of 1, the following formula is obtained from $\alpha$ and $\theta_o$ in the above (1), letting the length of the sort axis to be $\sqrt{Is}$;

$$I \propto \sqrt{Is} = \frac{|\sin 2\theta_o \sin\alpha|}{1 + \sqrt{1 - \sin^2 2\theta_o \sin^2\alpha}} \quad (1)$$

The ratio in the biaxial model is expressed using the angle $\theta_o$ which is different from the angle $\theta$ used in the case of the uniaxial model. ($\sqrt{Is} \propto |\sin 2\theta \sin\alpha|$: in the uniaxial model)

This is because the directions of the refractive indices n" and $n_3$ are not coincident with each other as viewed in the direction of the ray in the biaxial model (see FIG. 2).

(3) Calculation Formulae of Phase Difference $\alpha$ and Angle $\theta_o$

The substrate has the three main refractive indices when it shows the biaxial characteristics. Assuming these main refractive indices to be $n_1$, $n_2$, $n_3$, respectively, the index ellipsoid is given by:

$$\frac{x^2}{n_2^2} + \frac{y^2}{n_1^2} + \frac{z^2}{n_3^2} = 1 \quad (2)$$

Meanwhile, the phase difference $\alpha$ is expressed by:

$$\alpha = -\frac{2\pi}{\lambda}(n'' - n')h \quad (3)$$

Here, $\lambda$ is a wavelength of the incident light and h is a thickness of the substrate through which the incident light is transmitted.

In this case, the refractive indices n", n' correspond to the long axis and the short axis of the (elliptic) plane of the index ellipsoid sectioned by a plane perpendicular to the direction of the ray, respectively. FIG. 2 shows a conceptual (explanatory) view in this case. The refractive indices $n_1$, $n_2$, $n_3$ are orthogonal to one another, and the refractive indices n", n' are also orthogonal to each other.

Given a certain angle $\Psi$, the refractive indices n", n' can be calculated if the following two parameters are determined:

$\theta'$: angle formed by the intersecting line (OR in FIG. 3) between the direction of the ray and the plane including the direction of the long axis and the intersecting line (OP in FIG. 3) between the direction of the long axis and the plane including the radial direction, in the plane perpendicular to the long axis of the index ellipsoid, $\phi'$: angle between the normal to the direction of the long axis of the index ellipsoid and the direction of the ray in the plane including the direction of the long axis of the index ellipsoid Using the above angle $\theta'$, the formula (2) is subjected to transformation of the coordinate system. For this purpose, the direction of the ray is fixed to be vertical on the drawing sheet and the radial direction is fixed to be horizontal thereon.

Figure 4:
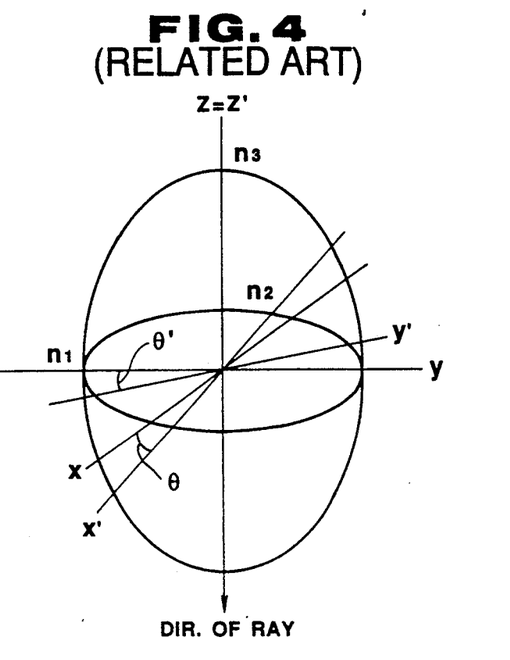
FIGS. 4 through 6 are explanatory views showing the coordinate axes for respective transformation of coordinate systems.

The transformation formulae between the coordinate system (x, y, z) and the coordinate system (x', y', z'=z) shown in FIG. 4 are given by:

$$x = x' \cos\theta - y' \cos\theta$$

$$y = x' \sin\theta + y' \sin\theta$$

$$z = z'$$

By putting the above formulae into the formula (2):

$$\left(\frac{\cos^2\theta'}{n_2^2} + \frac{\sin^2\theta'}{n_1^2}\right)x'^2 + 2\left(\frac{1}{n_1^2} - \frac{1}{n_2^2}\right)\sin\theta'\cos^2\theta'x'y' + \left(\frac{\sin^2\theta'}{n_2^2} + \frac{\cos^2\theta'}{n_1^2}\right)y'^2 + \frac{2}{n_3^2}z'^2 = 1 \quad (4)$$

Figure 5:
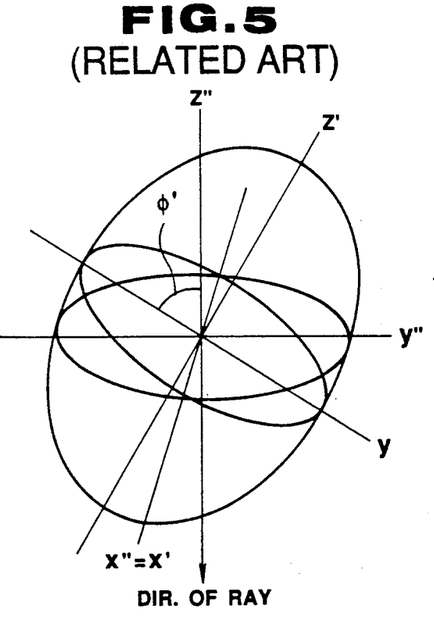

Then, another transformation is made to rotate the coordinate system through the angle $\phi'$ about the x' axis, as shown in FIG. 5. Thus, the following transformation formulae between the coordinate system (x', y', z') and the coordinate system (x", y", z");

$$x' = x''$$

$$y' = y'' \sin\phi' - z'' \cos\phi'$$

$$z' = y'' \cos\phi' + z'' \sin\phi'$$

are put into the formula (4) along with z"=0, which results in:

$$\left(\frac{\cos^2\theta'}{n_2^2} + \frac{\sin^2\theta'}{n_1^2}\right)x''^2 + 2\left\{\frac{\cos^2\phi'}{n_3^2} + \left(\frac{\sin^2\theta'}{n_2^2} + \frac{\cos^2\theta'}{n_1^2}\right)\sin\phi'\right\}y''^2 + 2\left(\frac{1}{n_1^2} - \frac{1}{n_2^2}\right)\sin\theta'\cos\theta'\sin\phi'x''y'' = 1 \quad (5)$$

Figure 6:
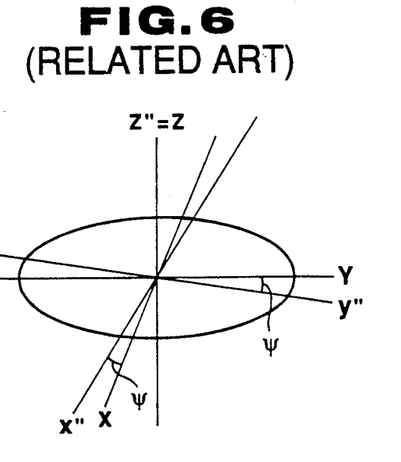

This formula represents an ellipse of the index ellipsoid sectioned by a plane including the refractive indices n", n' and perpendicular to the direction of the ray. In order to determine the directions of the long and short axes of this ellipse, still another transformation is made to rotate the coordinate system through the angle $\psi$ about the z" axis, as shown in FIG. 6. Thus, by using the following transformation formulae between the coordinate system (x", y", z") and the coordinate system (X, Y, Z);

$$x'' = X \cos \psi - Y \sin \psi$$

$$y'' = X \sin \psi - Y \cos \psi$$

$$z'' = Z$$

and by putting;

$$A = \frac{\cos^2 \theta'}{n_2^2} + \frac{\sin^2 \theta'}{n_1^2} \tag{6}$$

$$B = \frac{\cos^2 \phi'}{n_3^2} + \left( \frac{\sin^2 \theta'}{n_2^2} + \frac{\cos^2 \theta'}{n_1^2} \right) \sin \phi' \tag{7}$$

$$C = 2 \left( \frac{1}{n_1^2} - \frac{1}{n_2^2} \right) \sin \theta' \cos \theta' \sin \phi' \tag{8}$$

the formula (5) is rewritten to:

$$(A \cos^2 \psi + B \sin^2 \psi + C \sin \psi \cos \psi) X^2 + (A \sin^2 \psi + B \cos^2 \psi - C \sin \psi \cos \psi) Y^2 + \{2(B - A) \sin \psi \cos \psi + C (\cos^2 \psi - \sin^2 \psi)\} XY = 1 \tag{9}$$

The refractive indices n" and n' correspond to the lengths of the long and short axes of this ellipse, respectively, as given when it becomes the standard form. In order that the ellipse represented by the formula (9) becomes the standard form, the coefficient of the XY term must be zero (0). That is to say:

$$\{2(B-A) \sin \psi \cos \psi + C (\cos^2 \psi - \sin^2 \psi)\} XY = 0$$

This is rearranged to:

$$\frac{C}{A - B} = \tan 2\psi \tag{10}$$

$$\therefore \psi = \frac{1}{2} \tan^{-1} \left( \frac{C}{A - B} \right)$$

Using the above angle $\psi$, the refractive indices n', n" can be determined as follows:

$$n' = \frac{1}{\sqrt{A \cos^2 \psi + B \sin^2 \psi + C \sin \psi \cos \psi}} \tag{11}$$

$$n'' = \frac{1}{\sqrt{A \sin^2 \psi + B \cos^2 \psi - C \sin \psi \cos \psi}} \tag{12}$$

Figure 3:
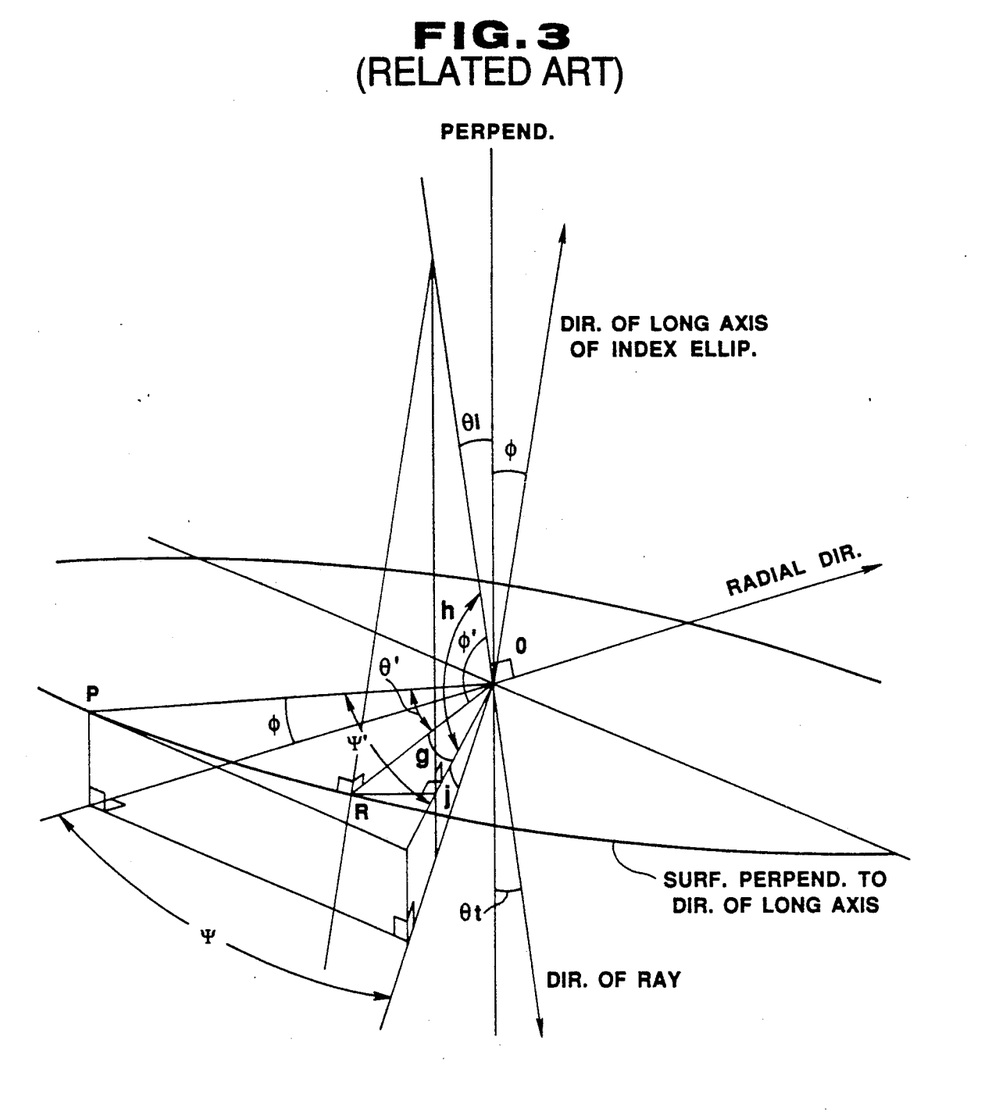

Note that the above mentioned angles $\theta'$ and $\phi'$ can be determined geometrically in FIG. 3. That is to say, from both the relation formulae;

$$\cos \Psi' = \frac{\cos \Psi}{\cos \phi \sqrt{1 + \tan^2 \phi \cos^2 \Psi}}$$

$$\cos g = \frac{\sin \theta t + \cos \theta t + \tan \phi \cos \Psi}{\cos \chi \sqrt{1 + \tan^2 \phi \cos^2 \Psi}}$$

and the geometrical relation in FIG. 3;

$$\theta' = \Psi' - g$$

$\theta'$ is given by:

$$\theta' = \cos^{-1} \left( \frac{\cos \Psi}{\cos \phi \sqrt{1 + \tan^2 \phi \cos^2 \Psi}} \right) + \cos^{-1} \left( \frac{\sin \theta t + \cos \theta t + \tan \phi \cos \Psi}{\cos \chi \sqrt{1 + \tan^2 \phi \cos^2 \Psi}} \right) \tag{13}$$

On the other hand, the angle $\phi'$ can be determined below using the cosine theorem:

$$\phi' = \sin^{-1} (\cos \theta t \cos \phi - \cos \Psi \sin \theta t \sin \phi) \tag{14}$$

It is to be noted that while the angles $\theta$ and $\theta_o$ are equal to each other in the uniaxial model, they are generally different in the biaxial model. The relation formula between those two angles is given below using the angle $\psi$ determined from the formula (10):

$$\theta_o = \theta - \psi \tag{15}$$

As represented by the formula (11) in the above cited U.S. Pat. No. 4,792,227, $\theta$ is given by:

$$\theta = \tan^{-1} \left( \frac{\sin \Psi \sin \phi}{-\sin \theta t \cos \phi + \cos \theta t \cos \Psi \sin \phi} \right) + \tan^{-1} \left\{ \frac{\cos(\theta i - \theta t)}{\tan \Psi \cos \theta i} \right\} \tag{16}$$

Therefore, $$\theta_o = \tan^{-1} \left( \frac{\sin \Psi \sin \phi}{\sin \theta t \cos \phi + \cos \theta t \cos \Psi \sin \phi} \right) + \tan^{-1} \left\{ \frac{\cos(\theta i - \theta t)}{\tan \Psi \cos \theta i} \right\} - \psi \tag{17}$$

Furthermore, in the above discussion, the formula (3) is as follows:

$$\alpha = -\frac{2\pi}{\lambda} (n'' - n')h \tag{3}$$

The formulae (11), (12) and (10) are put together as follows:

$$n' = \frac{1}{\sqrt{A \cos^2 \psi + B \sin^2 \psi + C \sin \psi \cos \psi}} \tag{11}$$

$$n'' = \frac{1}{\sqrt{A \sin^2 \psi + B \cos^2 \psi - C \sin \psi \cos \psi}} \tag{12}$$

-continued $$\psi = \frac{1}{2} \tan^{-1}\left(\frac{C}{A-B}\right) \quad (10)$$

From the above result, it will be found that the angles $\theta_o$ and $\alpha$ are functions each including $\Psi$, $\phi$, $\theta i$, $\theta t$, $n_1$, $n_2$ and $n_3$ as parameters, and Is also has the same parameters in accordance with the formula (1).

As represented by the formula (20) in U.S. Pat. No. 4,792,227, the light intensity in the direction of the short axis is determined below:

$$I = Is/(1+Is) \quad (18)$$

Thus, I is also a function of $\Psi$, $\phi$, $\theta i$, $\theta t$, $n_1$, $n_2$ and $n_3$.

Figure 7:
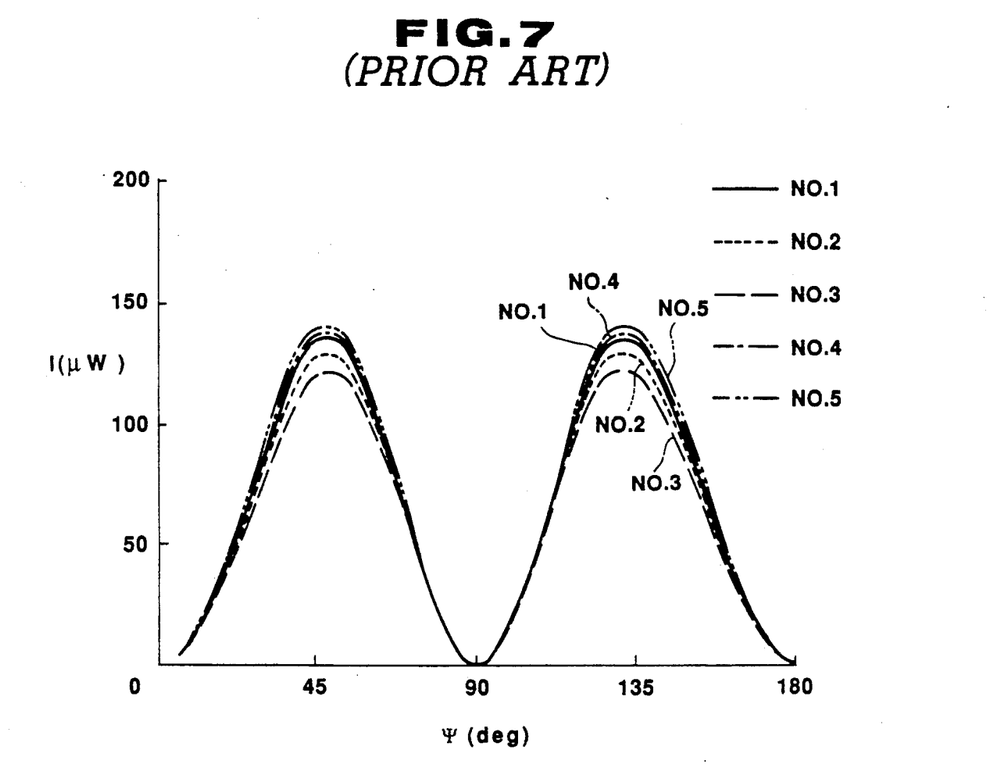
FIG. 7 is a graph showing the relationship between the light intensity and an azimuth as obtained from the theoretical formula fit for extension of the content of the above publication to the case of the three main refractive indices.

Given $\phi = 0°$, $\theta i = 30°$ and $\sin \theta t = \sin \theta i/n$ (where n is the refractive index of the substrate and assumed to be 1.5806), FIG. 7 plots the values of I for respective combinations No. 1–5 of the refractive indices $n_1$, $n_2$, $n_3$ shown in the following Table 1, with respect to the angle $\Psi$ of which value is varied in a range from 0° to 180°.

TABLE 1

| No. | $N_3(=n_3)$ | $N_2(=n_2)$ | $N_1(=n_1)$ |
|---|---|---|---|
| 1 | 1.58060 | 1.58000 | 1.58000 |
| 2 | " | " | 1.58001 |
| 3 | " | " | 1.58002 |
| 4 | " | 1.58001 | 1.58000 |
| 5 | " | 1.58002 | " |

With the method of the above cited U.S. Pat. No. 4,792,227, i.e., with the method in which the refractive indices are measured by varying the direction of an incoming linearly polarized light with the incident angle of the linearly polarized light held constant, the angle between the incident plane and the polarized plane is varied upon changes of the azimuth. This method is very effective in the case where the main refractive index $N_3$ in the direction perpendicular to the surface of the disc substrate is larger than $N_1$, $N_2$, to determine the magnitude of $|N_3 - N_1|$, i.e., the difference between the two main refractive indices in the thickness direction of the disk substrate and the planar direction thereof, but it tends to be inaccurate in the case of measuring the difference $(N_2 - N_1)$ between the two refractive indices $N_1$ and $N_2$ both in the planar direction.

FIG. 7 supports that point. More specifically, the graphs in FIG. 7 vary little in their forms from one another even if the two refractive indices $N_1$, $N_2$ are changed to a small extent with the refractive index $N_3$ held at a fixed value. The method of U.S. Pat. No. 4,792,227 is to compare the graph resulted from the experiment with the graph derived from the theoretical formula while changing the values of parameters in the theoretical formula appropriately, and then adopt the values of parameters, as measured values, which are given when both the graphs show best coincidence or match therebetween.

Therefore, due to a small difference between the refractive indices $N_1$, $N_2$ it is difficult to precisely determining the value of $|N_3 - N_1|$.

OBJECTS AND SUMMARY OF THE INVENTION

It is an object of this invention to provide a method of detecting the refractive index of a substrate for an optical disc whereby the difference between the two refractive indices in the planar direction of the substrate surface can be determined precisely.

Another object of this invention is to provide an apparatus for measuring the refractive index of a substrate for an optical disc whereby the difference between the two refractive indices in the planar direction of the substrate surface can be determined simply.

Figure 8:
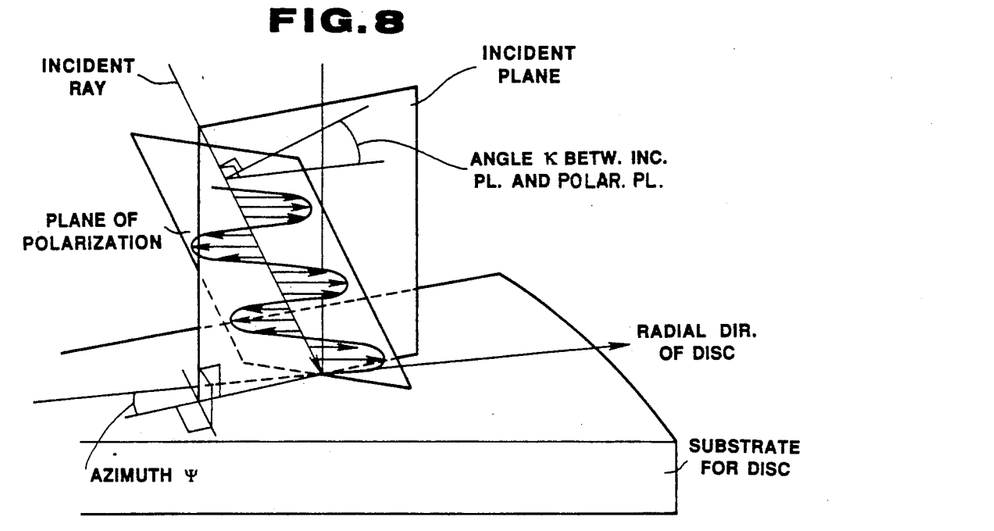
FIGS. 8 and 9 are explanatory views showing the relationship between an incident ray impinging upon a substrate, the incident plane, the polarized plane and other elements to explain a method according to the first embodiment.

With this invention, as shown in FIG. 8 basically in the form of a explanatory view, a linearly polarized light beam is incident at an angle on a substrate for a disc where the angle is not a right angle, but at an oblique angle with respect to the substrate surface, while holding an angle $\kappa$ constant between the plane of polarization of the linearly polarized light and the incident plane. The intensity of the leaked light passing through an analyzer, set in a crossed Nichol state with respect to the linearly polarized light, is measured while changing an angle (referred to as an azimuth angle $\Psi$) between the incident plane and a reference line, such as a line extending in the radial direction of the disc substrate. These measured values are compared with the calculated values derived from the theoretical formula for determining the respective magnitudes of the three refractive indices.

As a result, the index ellipsoid can be determined.

BRIEF DESCRIPTION OF THE DRAWINGS

FIGS. 8 through 14 are concerned with a first embodiment of this invention in which;

FIG. 10 illustrates an apparatus according to the first embodiment in which FIGS. 15 through 16 are concerned with a second embodiment of the present invention in which;

DETAILED DESCRIPTION OF PREFERRED EMBODIMENTS

As shown in FIG. 10, a refractive index measuring apparatus 1 according to the method of the first embodiment includes a He-Ne laser 2 as a light source for producing a coherent ray. A laser beam emitted from the He-Ne laser 2 is converted to a linearly polarized light through a polarizer 3 and then incident on a substrate for an optical disc (or disc substrate) 5 mounted on a rotatable stage (referred to as a $\theta$-stage hereinafter).

The He-Ne laser 2 has a beam diameter of about 1 mm and may be of a commercially available one so long as it meets the above requirement.

The He-Ne laser 2 or the $\theta$-stage 4 are set up in such a manner that the laser beam goes across (intersects) the center of rotation of the $\theta$-stage 4. The disc substrate 5 to be measured is mounted on the disc-like $\theta$-stage 4 such that the intersecting point becomes an incident point of the laser beam on the disc substrate 5.

In addition, the laser beam is inclined from the normal direction with respect to the disc substrate 5 to provide an incident angle $\theta i$ ($-90° < \theta i < 90°$).

The $\theta$-stage 4 has an opening 4a formed at the center. The laser beam having transmitted through the disc substrate 5 passes through the opening 4a and enters an analyzer 6 set in a crossed Nichol state with respect to the polarizer 3. The laser beam (leaked light) having passed through the analyzer 6 is received by a photo detector 7.

Supposing now that the He-NE laser 2, the polarizer 3, the analyzer 6 and the photo detector 7 are placed on a horizontal surface plate, for example, and arranged along an optical path of the laser beam, i.e., aligned along a straight line. In this case, the $\theta$-stage 4 is vertically disposed on the horizontal surface such that the stage surface is inclined by the incident angle $\theta i$ with respect to the optical path. This state can be seen from the plan view of FIG. 10a and the front view of FIG. 10b.

Figure 10A:
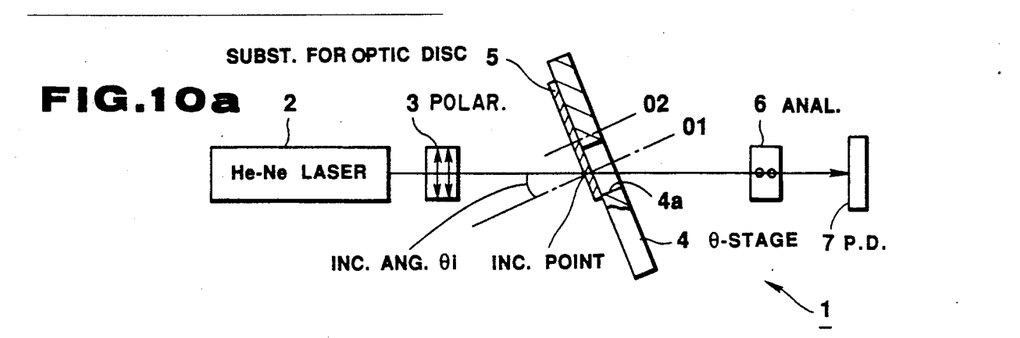
FIG. 10a is a plan view and FIG. 10b, 10c and 10d are front views.

At this time, the incident plane, i.e., the plane including the normal to the disc substrate 5 at the incident point and the incident laser beam, lies always horizontal independently of a degree of the incident angle $\theta i$ or a rotation angle of the $\theta$-stage 4 (the incident plane is parallel to the drawing sheet in FIG. 10a). The incident plane is perpendicular to the drawing sheet in FIG. 10b. This geometrical relationship is illustrated in FIG. 11A. Note that O1, O2 in FIG. 10a represent the central axes of the $\theta$-stage 4 and the disc substrate 5, respectively.

If the polarizer 3 is also set such that the polarized plane lies horizontal, an angle $\kappa$ between the incident plane and the polarized plane becomes 0°.

Furthermore, an angle between the incident plane and the radial direction of the disc, i.e., an azimuth $\Psi$, also becomes 0°.

Figure 10B:
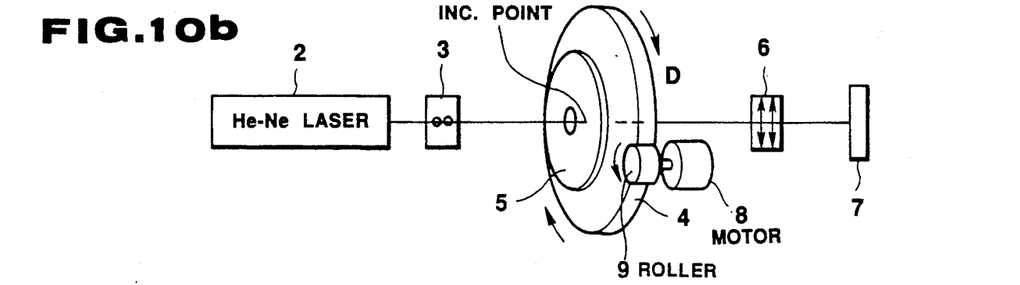
Figure 10C:
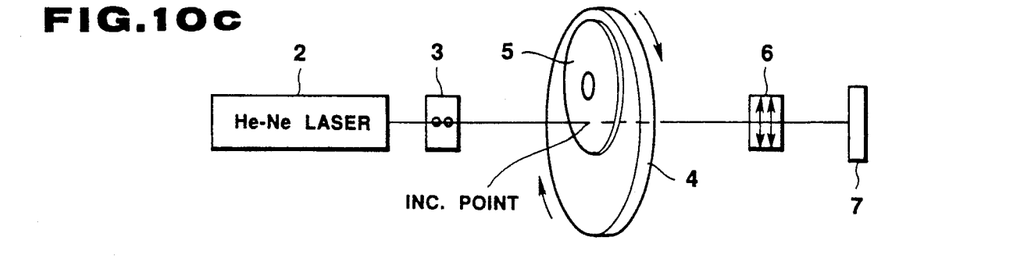
Figure 10D:
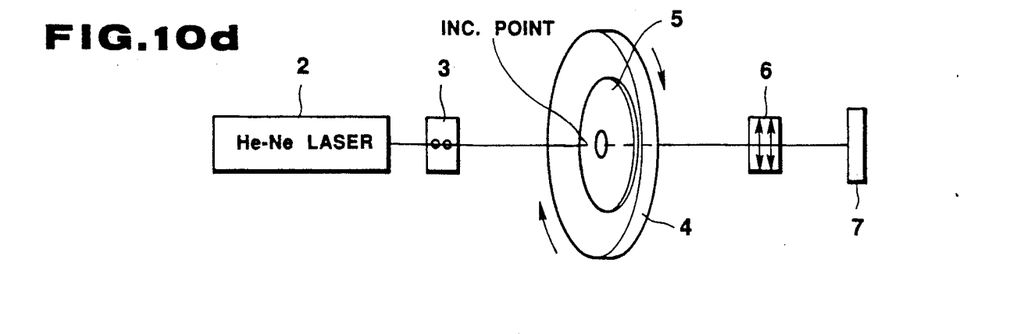
Figure 11A:
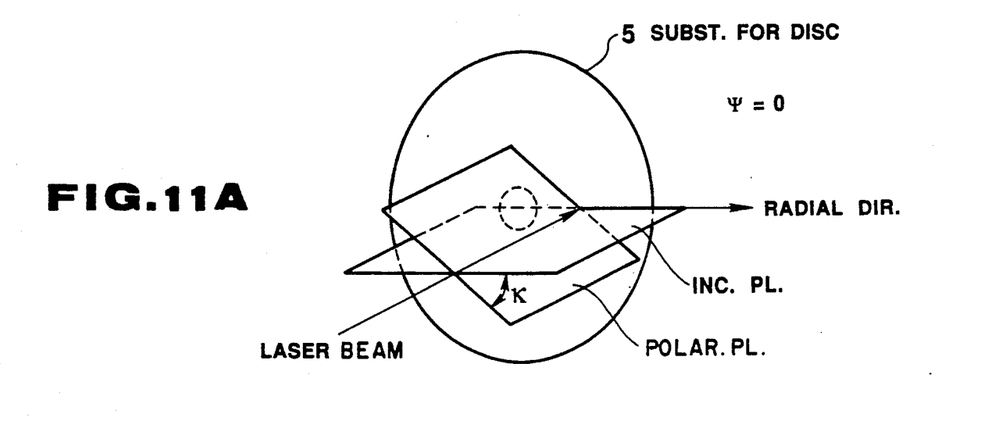
FIG. 11 is an explanatory view corresponding to FIG. 10, showing the relationship between the polarized plane, the incident plane, the radial direction and other elements.

As the $\theta$-stage 4 is rotated about its central axis O1 from the state shown in FIGS. 10a and 10b by driving a motor 8, for example, the motor 8 having a shaft, roller 9 held against the periphery of the $\theta$-stage 4 as shown in FIG. 10b, the radial direction of the disc or the disc substrate 5 is gradually rotated with the incident point of the disc substrate 5, the incident angle $\theta i$ and the incident plane remained unchanged (i.e., the center of the disc substrate revolves about the central axis O1 of the $\theta$-stage 4, following a circular path). Note that the $\theta$-stage 4 is rotatably supported with the aid of ball bearings disposed around the outer periphery of the $\theta$-stage. Accordingly, the angle between the incident plane and the radial direction (i.e., the azimuth $\Psi$) can be varied without changing the angle $\kappa$ between the incident plane and the polarized plane. Assuming that the azimuth is equal to zero, i.e., $\Psi = 0$, in FIG. 10b, when the $\theta$-stage 4 is rotated by 90° ($\pi/2$) from this state in the direction of arrow D, it comes into a state shown in FIGS. 10c and 11B with the azimuth $\Psi = \pi/2$. Further 90° ($\pi/2$) rotation brings the $\theta$-stage 4 into a state shown in FIGS. 10d and 11C with the azimuth $\Psi = \pi$.

Figure 11B:
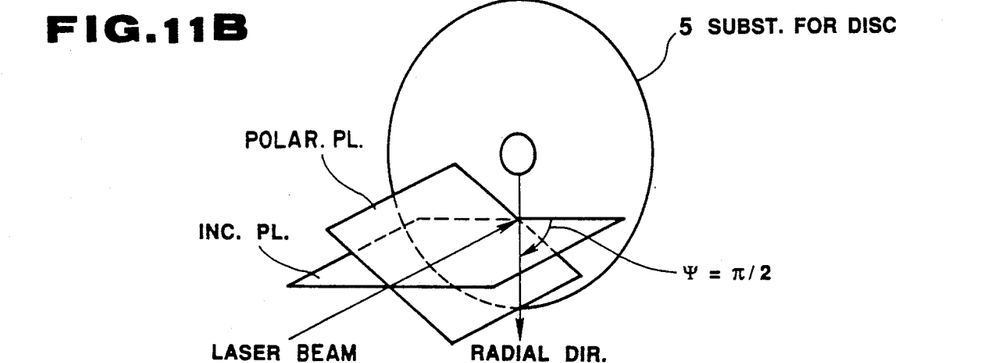
Figure 11C:
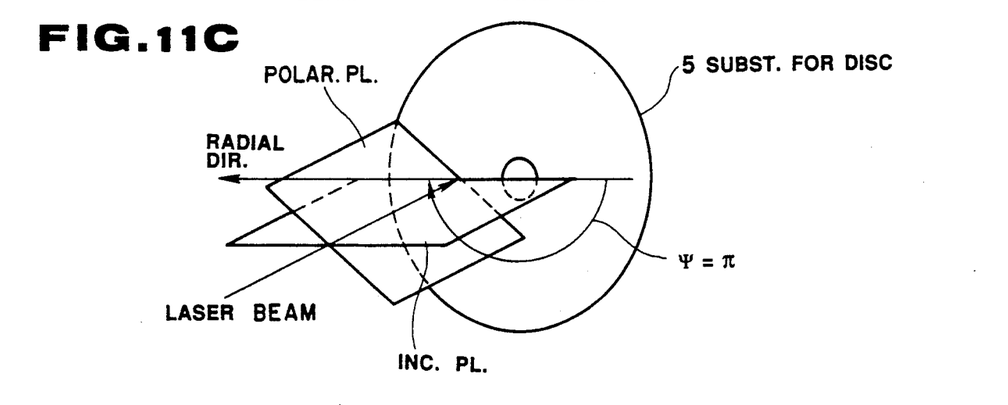

While the incident plane will remain horizontal even if the incident angle $\theta i$ is varied, so long as the $\theta$-stage 4 is held in a vertical state, the angle $\kappa$ between the incident plane and the polarized plane can arbitrarily be varied simply by rotating the polarizer 3 to change the polarized plane. FIG. 11 illustrates the geometrical relationship between the polarized plane, the incident plane and the radial direction as given when the $\theta$-stage 4 is rotated with the angle $\kappa$ held fixed. That is to say, FIG. 10b corresponds to FIG. 11A, FIG. 10c to FIG. 11B, and FIG. 10d to FIG. 11C, respectively.

Figure 9:
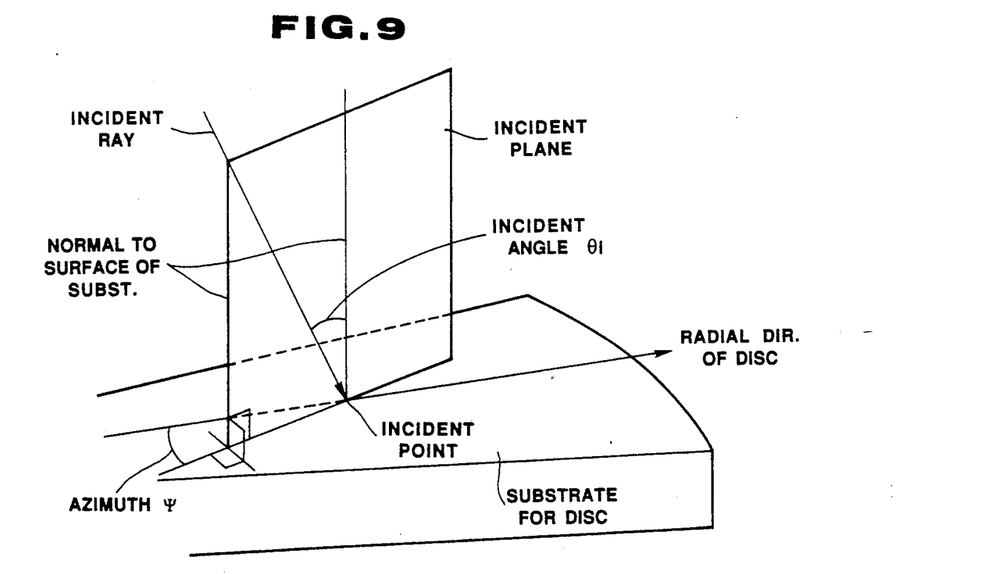

In FIGS. 11A, 11B and 11C, the azimuth $\Psi$ is varied from 0 to $\pi$ (180°) while holding constant the angle $\kappa$ between the incident plane and the polarized plane. During this time, the polarizer 3 and the analyzer 6 are held in a fixed state. The photo detector 7 measures the intensity of the leaked light passing through the analyzer 6 dependent on changes of the azimuth $\Psi$. In other words, the variable to be measured is the intensity of the light that is incident on the photo detector 7 when the azimuth $\Psi$ is varied with the angle $\kappa$ between the incident plane and the polarized plane held constant. The mutual relationship between the light incident on the photo detector 7, the incident plane, the polarized plane and the azimuth $\Psi$ is illustrated in FIG. 8. The azimuth $\Psi$ in FIG. 8 is also shown in FIG. 9.

Figure 12:
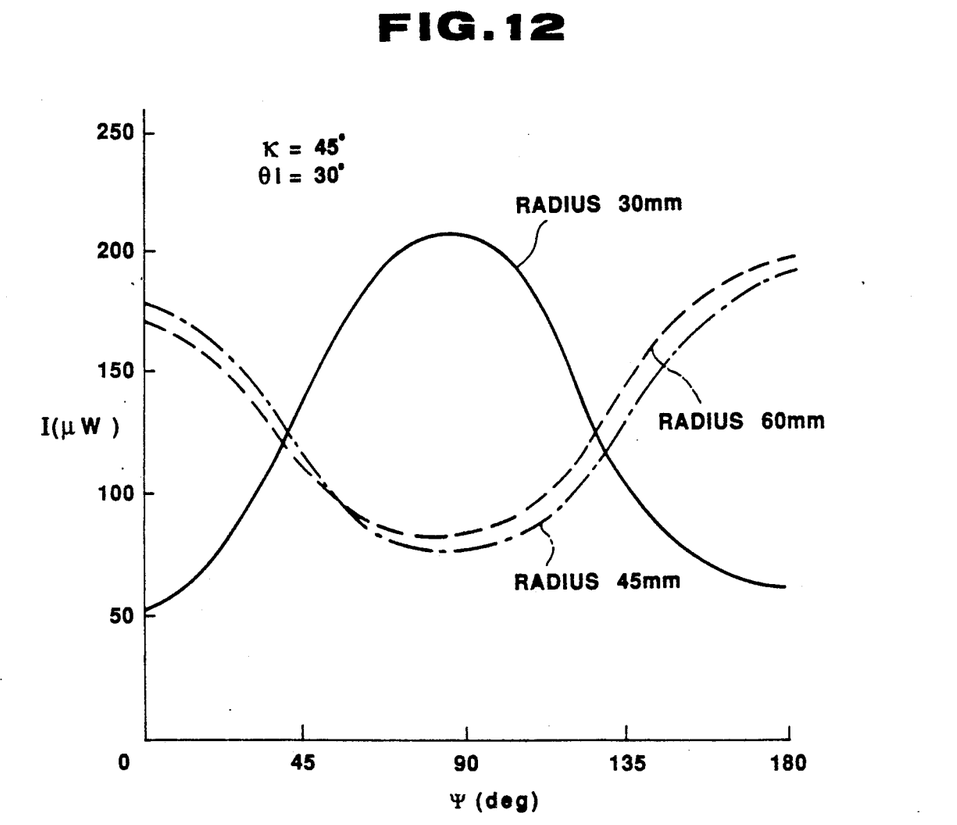
FIG. 12 is a graph showing the measured result.

FIG. 12 shows the result of measuring the intensity I of the leaked light passing through the analyzer 6 with respect to the varying azimuth $\Psi$ at three points on a polycarbonate substrate of $\phi 130$ corresponding to the radius 30 mm, 45 mm, 60 mm, respectively, assuming that the incident angle is 30° ($\theta i = 30°$) and the angle between the incident plane and the polarized plane is 45° ($\kappa = 45°$). In FIG. 12, the horizontal axis represents the azimuth $\Psi$. At the points of the radius 45 mm and 60 mm, the light intensity I comes to the maximum about $\Psi = 0°$, 180° and the minimum about $\Psi = 90°$.

In contrast, at the points of the radius 30 mm, the light intensity I comes to the minimum about $\Psi = 0°$, 180° and the maximum about $\Psi = 90°$.

Figure 13:
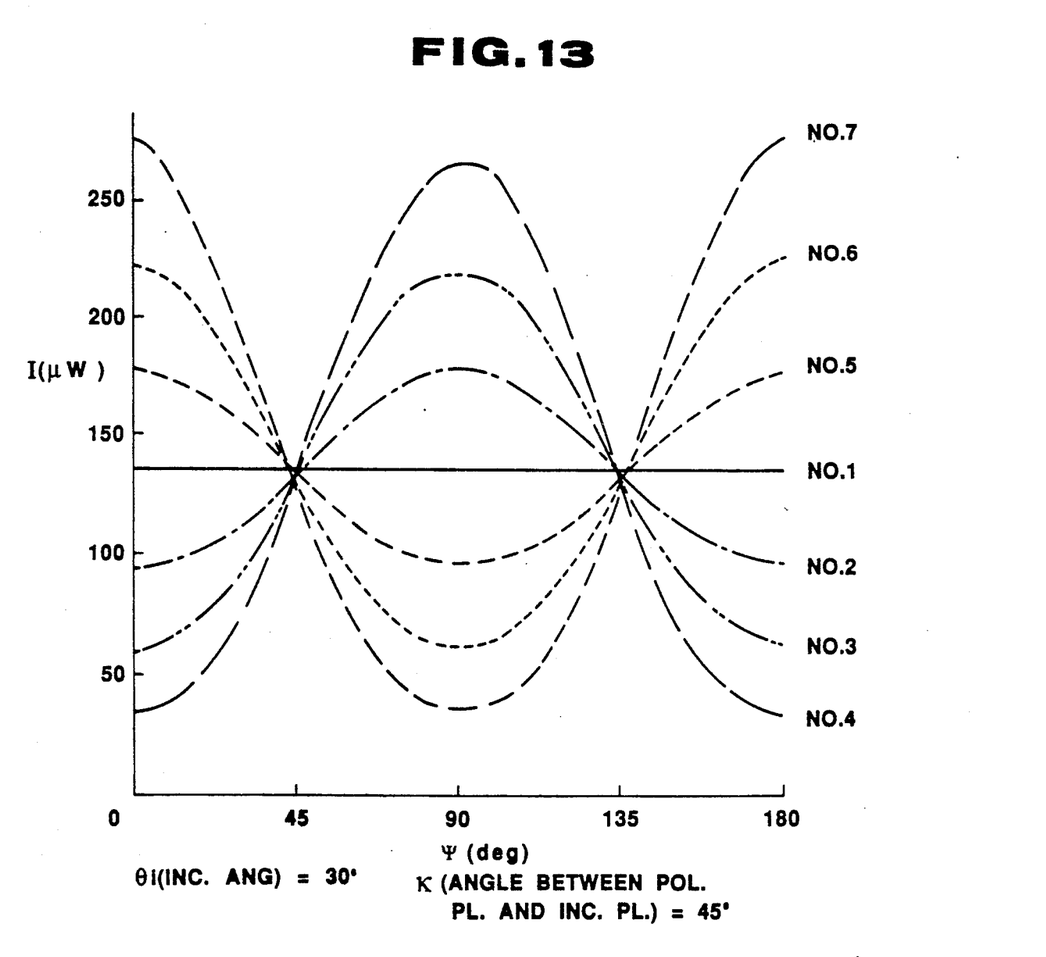
FIG. 13 is a graph showing curves of the theoretical formula according to the method of this embodiment.

The result of calculating the intensity I of the light passed through the analyzer 6 by variously setting the respective magnitudes of three main refractive indices of the index ellipsoid (as parameters) is plotted in FIG. 13.

More specifically, on the assumption that the main refractive index $N_3$ is perpendicular to the substrate surface, the main refractive index $N_2$ coincides with the radial direction of the substrate, and the main refractive index $N_1$ is perpendicular to the radial direction in the substrate surface, FIG. 13 represents the result of calculating the intensity I of the light having passed through the analyzer 6 by selecting the value of the main refractive index $N_3$ to be 1.5806 and then varying the values of the other two main refractive indices $N_1$ and $N_2$ so that the resulted curve best matches with that in the graph of FIG. 12.

The above calculation has been made on the same conditions as those in the foregoing actual measurement, i.e., under conditions of the incident angle $\theta i$ set to 30° and the angle $\kappa$ between the incident plane and the polarized plane set to 45°.

Further, the main refractive indices $N_3$, $N_2$, $N_1$ have been selected or set to the values listed in the following Table 2.

TABLE 2

| No. | $N_3$ | $N_2$ | $N_1$ |
|---|---|---|---|
| 1 | 1.58060 | 1.58000 | 1.58000 |
| 2 | " | 1.58000 | 1.58001 |
| 3 | " | 1.58000 | 1.58002 |
| 4 | " | 1.58000 | 1.58003 |
| 5 | " | 1.58001 | 1.58000 |
| 6 | " | 1.58002 | 1.58000 |
| 7 | " | 1.58003 | 1.58000 |

The comparison of FIG. 13 with FIG. 12 shows that the measured result in FIG. 12 at the point of radius 30 mm best matches with the curve No. 3 in FIG. 13 (i.e., the combination No. 3 in the Table 2). It will be thus found that the value of $|N_2|-|N_1|$ is on the order of $-2 \times 10^{-5}$ and the value of $|N_3|-|N_1|$ is on the order of $5.8 \times 10^{-4}$.

On the other hand, the measured result in FIG. 12 at the point of radius 30 mm, 60 mm apparently best matches with the curve of No. 5 in FIG. 13. It will be thus found from the numerals of $N_1$, $N_2$, $N_3$ in the Table 2 that the value of $|N_2|-|N_1|$ is on the order of $1 \times 10^{-5}$ and the value of $|N_3|-|N_1|$ is on the order of $6.0 \times 10^{-4}$ at the point of the radius 45 mm, 60 mm.

The process for obtaining the above calculated result and the calculation formulae will be described below. The calculation formulae can be resulted by slightly modifying the formulae shown in the section of the related art.

Figure 14:
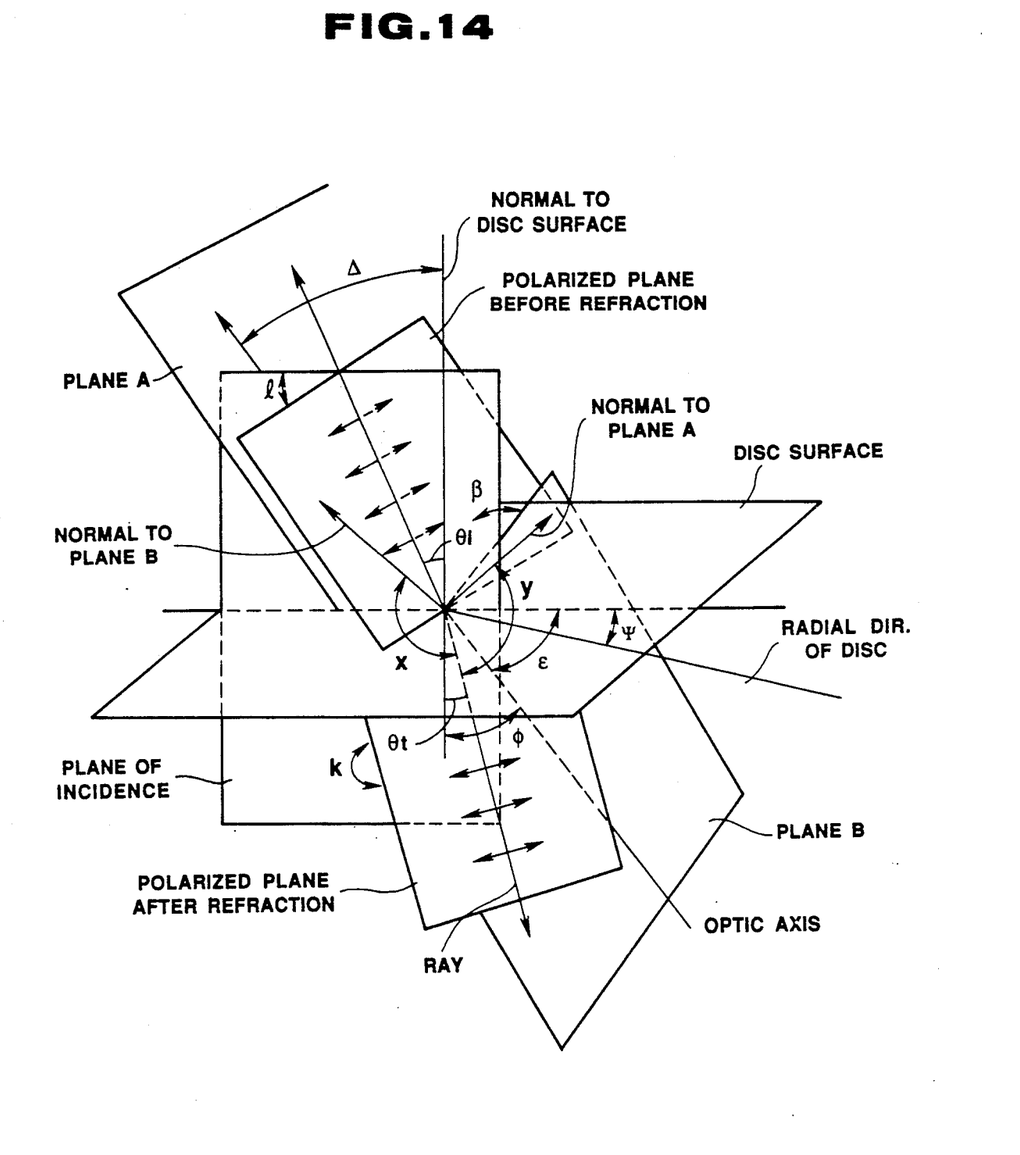
FIG. 14 is an explanatory view showing the relationship between the two polarized planes before and after refraction, when a light beam impinges upon the substrate.

The manner of deriving the formula corresponding to the above mentioned formula (16) is explained in U.S. Pat. No. 4,792,227, too. To begin with, respective angles are defined as shown in FIG. 14. That is to say:

$\epsilon$: angle between the optical axis and the incident plane
Y: angle between the polarized plane and the incident plane before refraction as viewed in the direction of the ray
$\kappa$: angle between the polarized plane and the incident plane after refraction as viewed in the direction of the ray
$\beta$: angle between the optical axis and the incident plane after refraction as viewed in the direction of the ray
$\theta t$: angle between the normal to the disc surface and the ray after refraction From the above definition, $$\theta = \beta + \kappa \quad (19)$$

On the other hand, $\kappa$ is given below from $\theta i$, $\theta t$ and the Fresnel's formula:

$$\tan \kappa = \cos(\theta i - \theta t) \cdot \tan Y$$

Accordingly:

$$\kappa = \tan\{\cos(\theta i - \theta r) \cdot \tan Y\} \quad (20)$$

Assuming that the optical axis is inclined by a certain angle with respect to the disc surface in the plane which includes the radial direction and a perpendicular to the disc surface, the angle $\phi$ between the normal to the disc surface and the optical axis as viewed in the radial direction is related to $\Psi$ and $\epsilon$ as follows:

$$\sin \epsilon = \sin \phi \cdot \sin \Psi \quad (21)$$

Assuming now that the angle between the surface (the plane A in FIG. 14) including the optical axis and a perpendicular to the incident plane and the normal to the disc surface is given by $\Delta$, this $\Delta$ is related to $\epsilon$ and $\Psi$ as follows:

$$\sin\Delta = \frac{\tan\epsilon}{\tan\Psi} \quad (21)$$

Furthermore, assuming that the angle between the normal (in the incident plane) to the surface including the optical axis and perpendicular to the incident plane and the direction of the ray after refraction is given by y, $\beta$ is related to $\epsilon$ and y as follows:

$$\tan\beta = \tan\epsilon \cdot \frac{1}{\cos y}$$

That is to say, by putting $y = \{\pi/2 - (\theta t + \Delta)\}$:

$$\tan\beta = \tan\epsilon \cdot 1/\sin(\theta t + \Delta) \quad (23)$$

From the formulae (21), (22) and (23):

$$\tan\beta = \frac{\sin\Psi\sin\phi}{\sin\theta t\cos\phi + \cos\theta t\cos\Psi\sin\phi} \quad (24)$$

Assuming that the polarized plane before convergence is normal to the radial direction, the following relationship holds:

$$\tan\gamma = \frac{\tan(\pi/2 - \Psi)}{\cos\theta i} \quad (25)$$

From the formulae (19), (20), (24) and (25), $\theta$ is therefore given by:

$$\theta = \tan^{-1}\left(\frac{\sin\Psi\sin\phi}{\sin\theta t\cos\phi + \cos\theta t\cos\Psi\sin\phi}\right) + \tan^{-1}\left\{\frac{\cos(\theta i - \theta t)}{\tan\Psi\cos\theta i}\right\} \quad (26)$$

where:

$$\theta t = \sin^{-1}(\sin\theta i/n)$$

In this embodiment, the angle $\kappa$ between the polarized plane and the incident plane is constant (e.g., 45°).

Taking it into account, the formula (26) can be rewritten to:

$$\theta = \tan^{-1}\left(\frac{\sin\Psi\sin\phi}{\sin\theta t\cos\phi + \cos\theta t\cos\Psi\sin\phi}\right) + \kappa \quad (27)$$

Accordingly, the angle $\theta_o$ is given by:

$$\theta_o = \theta - \psi \quad (28)$$

In addition, as shown in the formula (18), the light intensity I in the direction of the short axis is given by:

$$I = Is/(1+Is) \quad (29)$$

Thus, I is also a function of $\Psi$, $\phi$, $\theta i$, $\theta t$, $n_1$, $n_2$ and $n_3$. As with the formula (1), Is is given by:

$$I \propto \sqrt{Is} = \frac{|\sin 2\theta_o \sin\alpha|}{1 + \sqrt{1 - \sin^2 2\theta_o \sin^2 \alpha}} \quad (30)$$

Here, the angle $\theta_o$ in the formula for Is is expressed by the formula (28) using $\theta$ of the formula (27).

The actual main refractive indices of the substrate 5 can be determined from the values of the main refractive indices $N_1$, $N_2$, $N_3$ as parameters, by varying the azimuth $\Psi$ with the angle $\kappa$ between the polarized plane and the incident plane held constant, and then finding those values at which the measured value best matches the value derived from the theoretical formula shown in the formula (30).

According to the measuring method of this embodiment, as will be readily seen from the comparison thereof with that of the prior art (i.e., the comparison of FIG. 13 with FIG. 7), the changes of the light intensity resulted when varying the main refractive indices $N_1$, $N_2$ can be made much greater in FIG. 13 than in FIG. 7, making it possible to precisely determine the differences between the three main refractive indices $N_1$, $N_2$, $N_3$ of the index ellipsoid which are important in knowing the optical (physical) properties of the substrate for the optical disc.

Figures 15, 16:
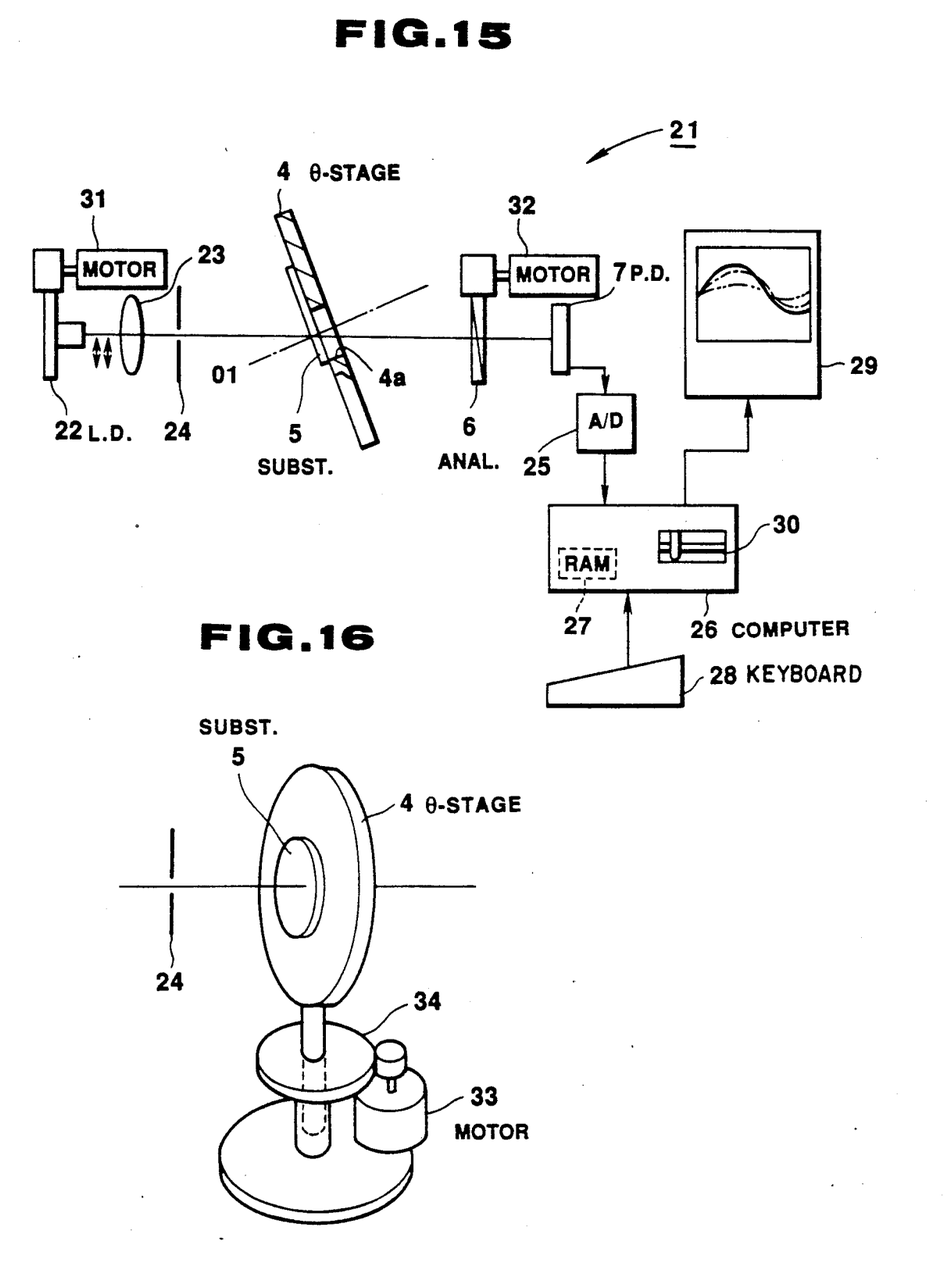
FIG. 15 is a plan view showing an apparatus according to the second embodiment.
FIG. 16 is a perspective view showing one example of means for setting a stage angle.

It is to be noted that the apparatus 1 of the first embodiment shown in FIG. 10 employs the He-Ne laser 2 as a light source, a semiconductor laser widely used in optical disc devices and the like may be employed to determine the refractive indices of the disc substrate for a wavelength of the semiconductor laser. A measuring apparatus 21 when using the semiconductor laser (or laser diode) is shown in FIG. 15.

A laser diode 22 emits a divergent light beam linearly polarized in a certain direction. This divergent light beam is collimated by a collimator lens 23 to become a parallel light beam, followed by passing a pin hole in a shield plate 24 and impinging upon a disc substrate 5 mounted on a $\theta$-stage 4. After having transmitted through the disc substrate 5, the light beam passes through an opening 4a in the $\theta$-stage 4 and enters an analyzer 6 held in a crossed Nichol state with respect to the linearly polarized light. The light beam having passed through the analyzer 6 is received by a photo detector 7. An output from the photo detector 7 after opto-electric conversion is turned by an A/D converter 25 into digital data which is then applied to a computer 26 for storage into a RAM 27, for example. This data can be indicated on a display 29 as plotted by a solid line, or recorded on a recording means such as a floppy disc 30, by inputting a proper command from a keyboard 28.

On the other hand, the theoretical data derived from the formula (30) is also recorded on the floppy disc 30, for example, so that they may be read out by operating the keyboard 28 and indicated as plotted by one-dot and two-dot chain lines with the main refractive indices $N_1$, $N_2$, $N_3$ varied as parameters. Accordingly, the main refractive indices $N_1$, $N_2$, $N_3$ can be determined by comparing the displayed curves of the measured and theoretical data and finding the values of those parameters whereby the curves best coincide with each other.

Although the first embodiment includes means for rotating the $\theta$-stage 4 to vary the azimuth $\Psi$, the laser diode 22 and the analyser 6 are driven for rotation by motors 31, 32, respectively, in a combined manner in the apparatus 21. Stated differently, the direction of the linearly polarized light incident on the substrate is varied by the motor 31, and the direction of polarization of the analyser 7 is held in a crossed Nichol state by the motor 32.

As shown in FIG. 16, for example, the $\theta$-stage 4 can be turned by a motor 33 which rotates its shaft roller held against a rotor 34, thereby setting the angle $\kappa$ between the polarized plane and the incident plane to any desired value. It should be understood that the angle $\kappa$ may be set manually. Note that a polarizer is not used in this embodiment.

Since the above mentioned detecting method and the measuring apparatus 21 can determine the differences between the three main refractive indices with a much higher accuracy than the prior art method represented in FIG. 7, the measurement may be carried out by changing the azimuth $\Psi$ and any other angle in a combined manner in such cases where lower accuracy will suffice (for example, the main refractive indices may be detected from comparison of the measured data, resulted by changing the azimuth $\Psi$ and the incident angle, with the theoretical data resulted by changing the incident angle).

The present invention is also applicable to light passing through the substrate two times. Thus, the light having transmitted through the substrate for the optical disc may be reflected by a reflecting member and the reflected light may be led to transmit through the substrate again but in the reversed direction, followed by detecting the returned light from the substrate.

Although the directions of the main axes of the main refractive indices have been presumed to be known in the above description, the magnitudes of the main refractive indices as well as the directions of the main axes thereof may be determined by measuring the light intensity I from the theoretical formula including the directions of the main axes of the main refractive indices as parameters, too, and then comparing the theoretical value with the measured value.

In addition, the substrate for the optical disc used in this invention is not limited to a magneto-optical recording medium, and it also means the substrate comprising an optical recording medium adapted to perform recording/reproducing in an optical manner.

In the above mentioned embodiment, the angle between the radial direction of the disc-like substrate 5 and the incident plane is prescribed as an azimuth $\Psi$ and this azimuth $\Psi$ is varied for the measurement. However, this invention can also be applied to a substrate other than a disc-like shape. In this case, for example, the azimuth $\Psi$ may be defined as an angle between the incident plane and an arbitrary line included in the substrate surface and passing an incident point on which the linearly polarized light beam impinges. Where a substrate in problem is shaped to have a point which can be regarded as the center, a line connecting the incident point and the center can be selected as the reference line.

Moreover, a still different embodiment can be arranged by combining the embodiments as mentioned above.

What is claimed is:

1. In a method wherein a linearly polarized light beam is incident on a substrate for a plate-like disc, light transmitted through said substrate for the disc is input to an analyzer set in a crossed Nichol state with respect to said linearly polarized light beam, and an intensity of a leaked light having passed through said analyzer is measured, a method of detecting a refractive index of said substrate for an optical disc, comprising the steps of:
 a first measurement process of measuring the intensity of the leaked light having passed through said analyzer by making said linearly polarized light beam incident on the surface of said substrate for the disc at an angle other than a right angle with respect to said substrate surface, while holding constant an angle between a plane of polarization of said linearly polarized light beam and an incident plane, said incident plane including a normal to the surface of the substrate at an incident point and the incident linear polarized light beam;
 a second measurement process of measuring the intensity of the leaked light having passed through said analyzer by changing an azimuth angle, defined as an angle between said incident plane and a reference line included in said substrate surface, while passing said linearly polarized light beam through the incident point at which said linearly polarized light beam impinges on said substrate surface;
 a comparison process of comparing the measurement intensities of the leaked light, obtained from said first and second measurement processes, with calculated values of the intensities of the leaked light obtained from a theoretical formal, said calculated values corresponding to the refractive index of the substrate; and
 a process for determining respective magnitudes of the three main refractive indices by obtaining the refractive index corresponding to the calculated values coinciding with the measured intensities.

2. A detecting method according to claim 1, wherein when said substrate has a disc-like shape, said reference line is a line extending in a radial direction to pass a center of said disc-like shape.

3. An apparatus for measuring a refractive index of a flat plate-like substrate for an optical disc, comprising:
 a light source for generating a light beam which is capable of being converged;
 polarizing means for polarizing said light beam into a linearly polarized light beam;
 angle setting means for setting an angle between (a) a plane of polarization of said linearly polarized light beam which is incident on said flat plate-like substrate having a refractive index which is to be measured and (b) an incident plane of said linearly polarized light beam on said flat plate-like substrate, said incident plane including a normal to a surface of the flat plate-like substrate at an incident point and the incident linearly polarized light beam;
 analyzer means on which the light transmitted through said substrate impinges, said analyzer means is arranged in a crossed Nichol state with respect to a direction of polarization determined by said polarizing means;
 photo detector means for receiving the light having passed through said analyzer means;
 azimuth changing means for changing an azimuth angle, defined as an angle between said incident plane and a reference line included in the surface of said substrate, while passing said linearly polarized light beam through an incident point at which said linearly polarized light beam impinges on said substrate surface, and while holding constant an angle between said plane of polarization and incident plane, and said azimuth changing means for holding said analyzer means in a crossed Nichol state;
 theoretical value outputting means for outputting theoretical values of light intensity with respective values of main refractive indices varied as parameters; and
 outputting means for determining coincidence between said theoretical values with measured values of the light intensity received by said photo detector means and for outputting the refractive index of said substrate corresponding to the coincidence.

4. A measuring apparatus according to claim 3, wherein when said substrate has a disc-like shape, said reference line is a line extending in a radial direction to pass a center of said disc-like shape.

5. A measuring apparatus according to claim 3, wherein said light source and said polarizing means comprise a semiconductor laser emitting a polarized light beam.

6. A measuring apparatus according to claim 3, wherein said angle setting means can manually set a plate surface of a stage, on which said substrate is mounted, at a certain angle with respect to an incident direction of said linearly polarized light beam.

7. A measuring apparatus according to claim 3, wherein said azimuth changing means comprises a motor for rotatively driving a stage on which said substrate is mounted.

8. A measuring apparatus according to claim 3, wherein said azimuth changing means comprises a motor for rotating said polarizing means while maintaining said analyzer means, in a crossed Nichol state with respect to a direction of polarization determined by said polarizing means.

9. A measuring apparatus according to claim 3, wherein said theoretical value outputting means comprises a computer.

* * * * *